United States Patent [19]

Williams

[11] Patent Number: Plant 5,306

[45] Date of Patent: Oct. 30, 1984

[54] MINIATURE ROSE PLANT 'BIT O' GOLD'

[76] Inventor: Ernest D. Williams, 1510 Lebanon Ave., Dallas, Tex. 75208

[21] Appl. No.: 376,919

[22] Filed: May 10, 1982

[51] Int. Cl.[3] ..... A01H 5/00

[52] U.S. Cl. ..... Plt./8

[58] Field of Search ..... Plt./8

*Primary Examiner*—James R. Feyrer

[57] ABSTRACT

The subject of the present disclosure is a new and distinct variety of miniature rose plant characterized by the clear bright yellow color of the flowers and by the profusion of bloom.

1 Drawing Figure

1

The present invention relates to a new and distinct variety of hardy, dwarf, bush type rose plant of the miniature class; the variety being primarily characterized—as to novelty—by small golden yellow flowers which in general color effect are similar to Golden Angel, a miniature variety (U.S. Plant Pat. No. 4,028).

The variety is further characterized by:

An abundance of bloom, with flowers borne singly or several to the stem in loose clusters.

Sweet light fragrance.

A plant which is vigorous, of rounded somewhat upright shape with semi-glossy to matt, small foliage, with pointed leaflets; the buds and flowers being similar in form and size to Gold Coin (miniature—U.S. Plant Pat. No. 2,921), but averaging less petals.

The plant, which has a normal height of about 12 inches, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Dallas, Tex., under conditions of careful control and observation, as a cross between an un-named seedling (miniature—not patented), as the seed parent and Golden Angel (miniature—U.S. Plant Pat. No. 4,028,), as the pollen parent.

Subsequent to origination of the variety I successfully reproduced it, at my nursery, located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature. Variety Name: Bit O'Gold.

Flowers borne: Usually singly — sometimes several together on slender wirey stems.

Quantity of bloom: Abundant both outside and in greenhouse.

Bud:

2

*Peduncle.*—Medium to short length; slender but sturdy; erect; medium green, sometimes tinted bronze (outdoors).

*Hairs.*—Fairly numerous.

*Before calyx breaks.*—Size — small. form short; pointed with several foliaceous apendages and few or no tiny hairs on surface of bud; with foliaceous parts extending beyond the top of the bud equal to one-half or more of its length. Color — medium green, occasionally tinted with bronze (outdoors).

*As calyx breaks.*—Color — yellow.

*Opening.*—Opens well in all weather.

Bloom:

*Size when fully open.*—Small, averaging about 25 mm (1").

*Petalage.*—Double — averaging about 40 petals, arranged regularly plus sometimes several small petaloids.

*Form.*—Imbricated, becoming more open in center, with petals reflexing loosely outward, and later at maturity, rolled loosely outward, and downward. Open flowers may show stamens.

Petals: Fairly thick; satiny on inside and on outside surface.

*Shape.*—Outside petals, broad lanceolate with small (short) acute tip; intermediate — broad lanceolate with rounded tip; inside — lanceolate with rounded tip.

Color: Newly opened flower from a plant grown outdoors (1981 season), Dallas, Tex.

*Outside petal.*—Outside surface — near Cadmium Orange 8/2 or Saffron Yellow 7/2. Inside surface — near Cadium Orange 8/2 or Saffron Yellow 7/2.

*Intermediate petal.*—Outside surface — similar to outside petal. Inside surface — similar to outside petal.

*Inner petal.*—Outside surface — similar to intermediate petal; inside surface — similar to intermediate petal. General color effect; newly opened flowers — rich gold yellow. Three days open — color similar to newly opened flowers but less brilliant. Behavior — opens well in all weather. Spent petals drop off. Flower longevity (May 1981) — plant in pot 6 — 8 days or longer. Cut flowers at living room temperature 4–5 days or longer.

Reproductive organs:

*Stamens.*—Few — often malformed.

*Filaments.*—Varying length, yellow.
*Anthers.*—Yellow.
*Pollen.*—Little or none.
*Pistils.*—Average number.
*Styles.*—Fairly even; medium to short length; bunched; color — greenish.
*Ovaries.*—All enclosed in calyx.
*Hips.*—None.
*Sepals.*—Permanent; spear shaped; recurved against peduncle.
*Seed.*—None.

Foliage:

*Leaves.*—Compound of five (sometimes three or seven) leaflets; quite small; leathery; semi-glossy to matt.
*Leaflets.*—Shape: broad, nearly oval; apex acute; base rounded or rounded acute. Margin serrate. Color: medium to dark green; new growth — normal (medium) green. Rachis: medium strength; upperside may have a few very tiny short prickles or hairs, grooved; underside sparsely thorny with few or no tiny prickles. Stipules: short; narrow to medium width; short to medium length; narrow points which turn out usually at about 45 degrees or less.

Growth:

*Habit.*—Dwarf; bushy; rounded; much branched.
*Growth.*—Free, vigorous; internodes short.
*Canes.*—Medium slender; sturdy.

*Main stems.*—Color: medium green.
*Thorns.*—Few; slender; hooked slightly downward; color — tan. Prickles — none. Hairs — none.
*Branches.*—Color: medium green. Thorns: few; medium length; slender; nearly straight, inclined downward. Medium oval base. Prickles: none. Hairs: none.

The miniature rose plant and its flowers as herein described may vary in slight detail due to climatic, soil and cultural conditions under which the variety may be grown; the present description being of the variety as grown at Dallas, Tex.

The following is claimed:

1. A new and distinct variety of miniature rose plant of hardy; dwarf; bushy; rounded; much branched habit, substantially as illustrated and described, characterized by buds and flowers of a rich gold yellow color, being of a shade (or range) generally near Cadmium Orange 8/2 to Saffron Yellow 7/2 (or similar), the buds and flowers resembling the variety Gold Coin (U.S. Plant Pat. No. 2,921) in form and size; and further characterized by a plant of vigorous and compact growth habit, easy to propagate from cuttings, with an abundance of small to medium size semi-glossy to matt foliage and an abundance of flowers borne singly or several to the stem in loose cluster.

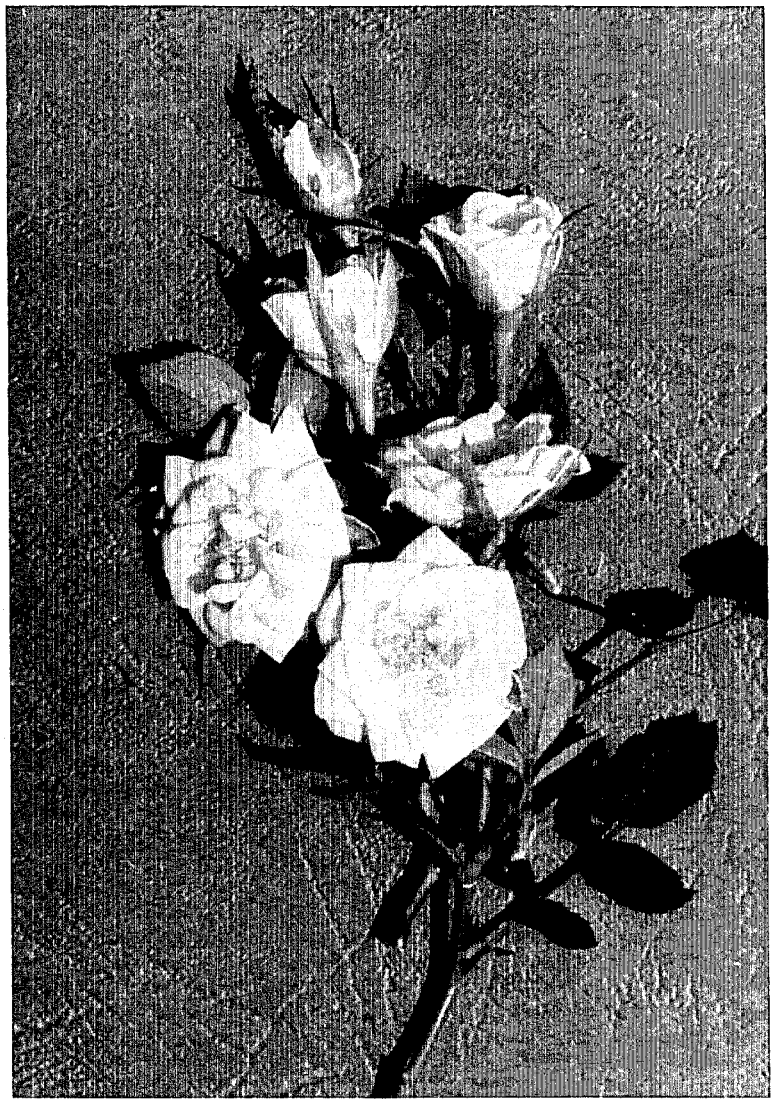

* * * * *